(12) United States Patent
Kindlein

(10) Patent No.: US 9,364,685 B2
(45) Date of Patent: *Jun. 14, 2016

(54) METHOD FOR IDENTIFYING THE LOCATION AT LEAST ONE TREATMENT CHANNEL FROM A GROUP OF A PLURALITY OF TREATMENT CHANNELS AS WELL AS A SYSTEM FOR EFFECTING RADIATION TREATMENT ON A PRE-SELECTED ANATOMICAL PORTION OF AN ANIMAL BODY

(75) Inventor: Johann Kindlein, Toenisvorst (DE)

(73) Assignee: NUCLETRON OPERATIONS B.V., Veenendaal (NL)

( * ) Notice: Subject to any disclaimer, the term of this patent is extended or adjusted under 35 U.S.C. 154(b) by 961 days.

This patent is subject to a terminal disclaimer.

(21) Appl. No.: 13/411,132

(22) Filed: Mar. 2, 2012

(65) Prior Publication Data

US 2012/0165595 A1 Jun. 28, 2012

Related U.S. Application Data

(63) Continuation of application No. 11/187,941, filed on Jul. 25, 2005, now Pat. No. 8,145,290.

(30) Foreign Application Priority Data

Jul. 18, 2005 (EP) .................................... 05076645

(51) Int. Cl.
*A61B 5/05* (2006.01)
*A61N 5/10* (2006.01)
*A61B 19/00* (2006.01)

(52) U.S. Cl.
CPC ............ *A61N 5/1007* (2013.01); *A61N 5/1048* (2013.01); *A61B 2019/5251* (2013.01); *A61N 2005/1008* (2013.01)

(58) Field of Classification Search
USPC .......................................... 600/407, 427, 428
See application file for complete search history.

(56) References Cited

U.S. PATENT DOCUMENTS 5,806,521 A 9/1998 Morimoto et al.
6,129,670 A * 10/2000 Burdette et al. .............. 600/427
(Continued)

FOREIGN PATENT DOCUMENTS

EP 1314451 5/2003
EP 1369143 12/2003
(Continued)

*Primary Examiner* — Joel F Brutus
(74) *Attorney, Agent, or Firm* — Finnegan, Henderson, Farabow, Garrett & Dunner LLP

(57) ABSTRACT

The invention relates to a method for identifying the location at least one treatment channel from a group of a plurality of treatment channels as wells as a system for effecting radiation treatment on a pre-selected anatomical portion of an animal body.
According to the invention the identifying method being characterized by the steps of
A selecting at least one of said plurality of treatment channels;
B reconstructing the actual location of said selected treatment channel relative to said animal body; and
C comparing said reconstructed location said pre-planned plurality of locations.
Furthermore the system according to the invention is characterized in that identifying means are present for identifying the location of at least one treatment channel from said group of said plurality of inserted treatment channels and comparing said identified location with one or more of said preplanned locations present in said treatment plan.

20 Claims, 3 Drawing Sheets

(56) References Cited

U.S. PATENT DOCUMENTS

Figure 1:
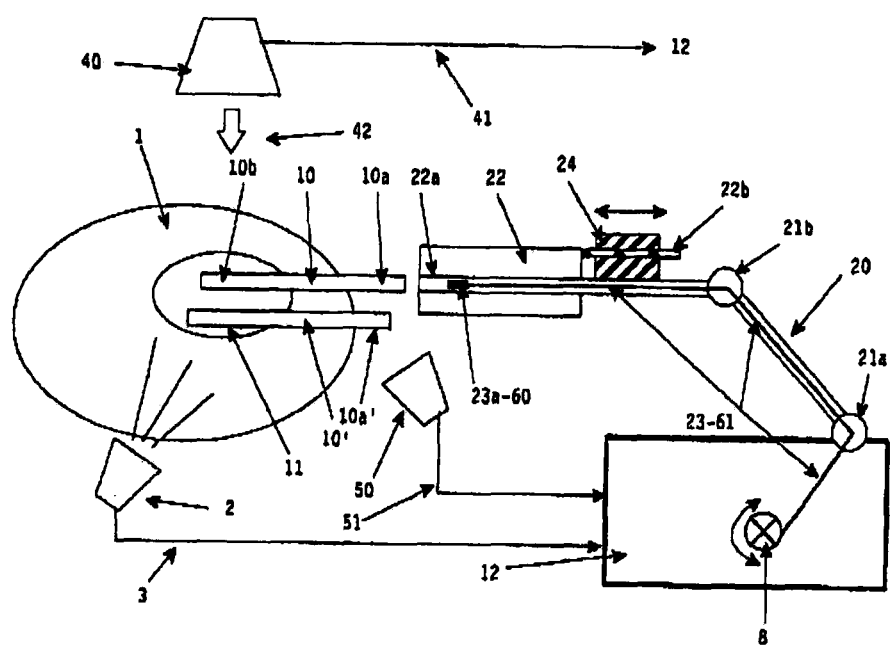

| | | |
|---|---|---|
| 6,311,084 B1 | 10/2001 | Cormack et al. |
| 6,546,279 B1 | 4/2003 | Bova et al. |
| 6,549,800 B1 | 4/2003 | Atalar et al. |
| 6,549,802 B2 | 4/2003 | Thornton |
| 6,731,966 B1 | 5/2004 | Spigelman et al. |
| 7,425,194 B2 | 9/2008 | Baltas et al. |
| 2002/0193677 A1 | 12/2002 | Thornton |
| 2002/0193685 A1 | 12/2002 | Mate et al. |
| 2003/0065260 A1 | 4/2003 | Cheng et al. |
| 2003/0100814 A1 | 5/2003 | Kindlein |
| 2003/0233123 A1 | 12/2003 | Kindlein et al. |

FOREIGN PATENT DOCUMENTS

| | | |
|---|---|---|
| EP | 1374949 | 1/2004 |
| EP | 1445002 | 8/2004 |
| EP | 1529533 | 5/2005 |

\* cited by examiner

METHOD FOR IDENTIFYING THE LOCATION AT LEAST ONE TREATMENT CHANNEL FROM A GROUP OF A PLURALITY OF TREATMENT CHANNELS AS WELL AS A SYSTEM FOR EFFECTING RADIATION TREATMENT ON A PRE-SELECTED ANATOMICAL PORTION OF AN ANIMAL BODY

This is a continuation of U.S. application Ser. No. 11/187,941, filed Jul. 25, 2005 which claims priority of European Application No. 05076645.0, filed Jul. 18, 2005, all of which are incorporated herein by reference.

The invention relates to a method for identifying the location at least one treatment channel from a group of a plurality of treatment channels already inserted at a plurality of locations within a pre-selected anatomical portion of an animal body, said treatment channels intended for guiding at least one energy emitting source from a radiation treatment apparatus within said anatomical portion for effecting radiation treatment according to an intended radiation dose distribution at specific positions and during specific times, wherein for each treatment channel its location within the anatomical portion of the animal body, the intended radiation dose distribution, the specific positions and the specific times are pre-planned during a treatment planning step.

The invention also relates to a system for effecting radiation treatment on a pre-selected anatomical portion of an animal body comprising
- first imaging means for generating image information of said pre-selected anatomical portion to be treated;
- processing means for generating a radiation treatment plan partly based on said image information for effecting said radiation therapy on said pre-selected anatomical portion, said treatment plan including information concerning:
  - a number, position and direction of a plurality of hollow treatment channels to be inserted within said anatomical portion;
  - one or more positions and corresponding times of one or more radiation emitting sources to be inserted through said plurality of hollow treatment channels;
  - the amount of radiation dose to be emitted;
- insertion means for inserting said plurality of hollow treatment channels at said planned positions and directions into said anatomical portion;
- radiation delivery means for inserting at least one energy emitting source through said plurality of hollow treatment channels at said one or more positions into said anatomical portion.

For brachytherapy using high dose rate (HDR) energy emitting sources, multiple treatment channels (catheters or hollow needles) are placed at specific orientations in a pre-selected target volume within an animal body and the treatment dose is delivered by positioning the high activity source at subsequent so-called dwell positions in each treatment channel during a specific amount of dwell time.

To this end each treatment channel is connected with an apparatus channel of the treatment apparatus through which interconnected channels the energy emitting source is guided from the treatment apparatus towards the intended pre-planned dwell positions within the inserted treatment channel for performing the brachytherapy treatment.

Imaging is commonly used to set the treatment margins and to optimize the dose distributions generated during the planning phase and are based on considerations, such as the channel orientations and desired dose tumour and critical organs.

However, human and computer errors during the treatment preparation process and the treatment can, potentially, place the dwell positions in a wrong orientation, resulting in treating the wrong target volume with the wrong treatment dose.

The orientation of each inserted treatment channel can be controlled by inserting a so-called dummy source from the treatment apparatus (e.g. an after loader apparatus) through the treatment channel and determining its orientation using an x-ray imaging device. However, such control method requires a capital investment of an x-ray imaging device and does not obviate possible mistakes by the hospital personnel when connecting a treatment channel inserted in the patient's body with an incorrect apparatus channel of the treatment apparatus.

These mistakes are not properly identified as presently known (remote controlled) brachytherapy treatment systems are unable to identify the right connection between inserted treatment channel and apparatus channel of the treatment apparatus.

To this end it is the aim of the invention to provide a method and system capable of identifying each treatment channel within a patient's body and connection of said treatment channel with the treatment apparatus.

To this end the identifying method is characterized by the steps of
A selecting at least one of said plurality of treatment channels;
B reconstructing the actual location of said selected treatment channel relative to said animal body; and
C comparing said reconstructed location with said pre-planned plurality of locations.

Moreover in an improved embodiment the method is characterized by step
D determining which of said pre-planned plurality of locations conforms said reconstructed location.

Yet another improvement resides in the fact that according to the invention the reconstruction step B involves the step of inserting through said selected treatment channel a tracking wire provided at its distal end with a tracking element.

More in particular the reconstruction step B involves the step of determining the location of an outer part of said selected treatment channel using vision techniques.

Furthermore the selection step A involves the step of
A1 connecting at least one of said plurality of treatment channels with at least one insertion channel of said treatment apparatus, whereas in an specific embodiment the connection step A1 involves the step of
A2 connecting said group of a plurality of treatment channels with said applicator channel apparatus by means of a template.

According to the invention the system is characterized in that identifying means are present for identifying the location of at least one treatment channel from said group of said plurality of inserted treatment channels and comparing using a special matching algorithm said identified location with one or more of said pre-planned locations present in said treatment plan.

Likewise in another embodiment for identifying purposes said identifying means are arranged in reconstructing the actual location of each of said plurality of inserted treatment channels relative to said animal body; and in comparing said reconstructed location with said pre-planned plurality of locations.

In one embodiment for identifying purposes said identifying means comprise a tracking element to be displaced through each of said plurality of inserted treatment channels using for example a tracking wire known from Northern Digital Inc. as the Aurora system or from Calypso Medical Inc. the Beacon transponder.

More in particular said tracking element is a magnetic tracking element being disposed at the distal end of said tracking wire, and during displacement of said magnetic tracking element through each of said plurality of inserted treatment channels the position of the tracking element is located.

With this embodiment it is possible to obtain an accurate information about the orientation of treatment channel being selected, which orientation can be compared with the pre-planned orientations of the treatment channels. Moreover a proper identification of the several treatment channels is obtained using a special matching algorithm, especially information with which apparatus channel each treatment channel is to be connected.

In another, yet versatile embodiment according to the invention said tracking element is an electromagnetic signal generating device.

In another embodiment said identifying means comprise second imaging means for imaging the location of a part of each of said plurality of inserted treatment channels extending out of said animal body.

In this embodiment each orientation of the inserted treatment channels is identified by means of a external vision technique.

Furthermore in a specific embodiment in order to establish a proper identification of the treatment channels being connected to the treatment apparatus all treatment channels are connected with said radiation delivery means through multiple delivery channels.

In another embodiment each of said plurality of treatment channels are arranged to be connected in a sequential order with said radiation delivery means through one single delivery channel. In this embodiment the single delivery channel is movable using a robotic arm controlled by information generated by said identifying means and said second imaging means.

For a proper connection of the treatment channel with the source delivery channel, the robotic arm is according to the invention provided with a connecting element, which is to be brought in contact with said part of said selected treatment channel extending out of said animal body.

More in particular said connecting element comprises a sensor for sensing the presence of said part of said selected treatment channel extending out of said animal body. This allows an accurate connection with the treatment channel without the risk of displacing the treatment channel within the patient's body thereby affecting its pre-planned orientation.

Yet another improvement of the system relates to a patient table far supporting the patient, said patient table can be orientated in three orthogonal directions, wherein said system further comprises a radiation dose monitoring probe device.

A fully automated and yet versatile system according to the invention is obtained as said system comprises planning means and controlling means and controlling means for controlling said first and second imaging means and said processing means and/or said insertion means and/or deliver means and/or identifying means and/or said patient table and/or said intracavitary radiation dose monitoring probe device.

Especially a compact system is realised as in another embodiment according to the invention said system is accommodated on a spatial ring shaped frame positioned around said patient to be treated.

Preferably said a spatial ring shaped frame has the configuration of a semi-ring.

Figure 2:
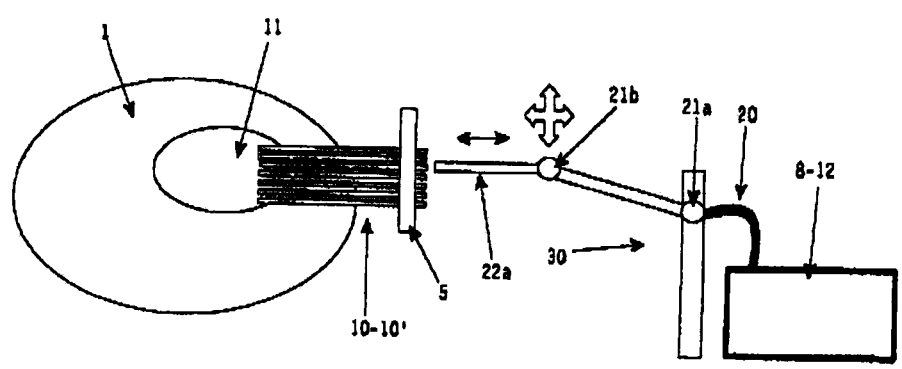
Figure 3:
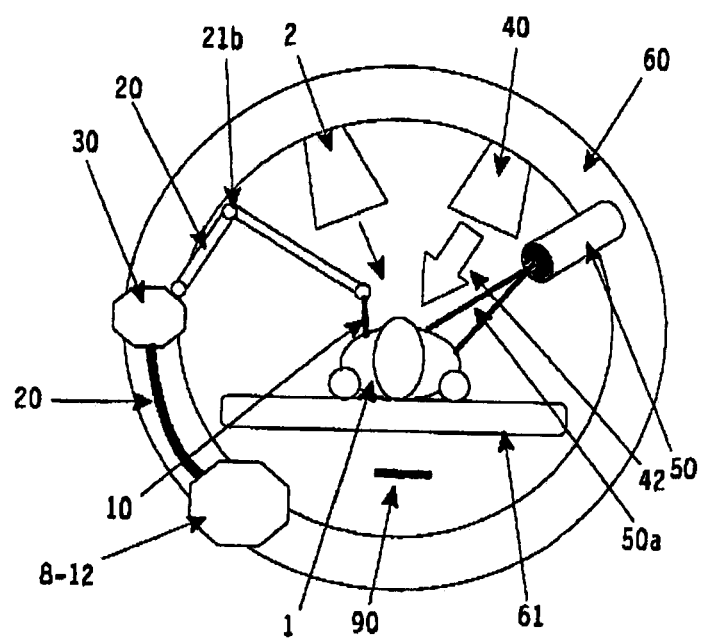

The invention shall now be described using a drawing showing in:

FIG. 1 a first embodiment of a system according to the invention;

FIG. 2 a second embodiment of a system according to the invention;

FIG. 3 a third embodiment of a system according to the invention.

It is to be noted that the following detailed description will be made with respect to treatment of a prostate gland. However, the device and method according to the invention can be used for each medical application, wherein a needle is to be inserted into an animal body using imaging means. The device and method described in this patent application can also be used as biopsy devices, and in far more applications wherein High Doses Radiation or Low Doses Radiation therapy is applied to an animal body. Therefore the description below should be regarded as an illustration for one specific application and not as a limitation of the invention.

In the prior art a large number of hollow needles or stylets 10-10' are all implanted at different locations in e.g. the prostate gland 11 of a male patient 1. These needles 10-10' remain a certain time period inside the patient's body 1 as the needles are connected permanently with the after loading apparatus 12 for inserting the energy emitting sources into each needle. The hollow needles 10-10' are connected manually by the hospital personnel with the apparatus channel(s) 20 of the treatment apparatus 8. Through said interconnected channels 20-10-10' the energy emitting sources 60 are guided from the multiple treatment channel connector module (indexer) of the treatment apparatus 12 towards the intended pre-planned dwell positions within the inserted treatment channel for performing the brachytherapy treatment as known in the prior art.

The connection by hand by the hospital personnel of the hollow needles with the apparatus channels of the treatment apparatus may introduce possible mistakes in the event that a hollow needle or treatment channel as inserted in the patient's body is connected with the incorrect apparatus channel of the treatment apparatus.

Such non-excluding personal mistakes may have severe consequences for the subsequent radiation treatment to be performed, as with the incorrect connection of a treatment channel with the multiple treatment channel connector module of the treatment apparatus 12 the energy emitting source from the radiation delivering means 8 is guided through the treatment channel at incorrect positions and at incorrect treatment intervals (due to the use of incorrect planning parameters) relative to the target tissue 11 to be treated.

According to the invention the method and apparatus provide a solution for this problem. With the method and apparatus according to the invention a new improved identification procedure is obtained allowing the proper identification of a treatment channel from a group of treatment channels already inserted within a patient's body such that based on the exact identification the correct therapy treatment as preplanned is performed on that treatment channel, meaning that after the proper identification the respective treatment channels are loaded with the energy emitting source according to the correct treatment planning parameters irrespective with which applicator channel they are connected.

The method according to the invention makes use of the following procedure: connecting a treatment channel, an applicator channel of the treatment apparatus reconstructing the actual location of said selected treatment channel relative to the patient's body, comparing using a matching algorithm said reconstructed location with the preplanned plurality of locations of the plurality of treatment channels used and determining which of said preplanned plurality of locations conforms with the reconstructed location.

With this identification procedure it is no longer required to make the correct connection (as pre-planned) of each treatment channel with the correct apparatus channel as each inserted treatment channel (hollow needle) is now properly identified thereby obviating a treatment using incorrect planning parameters.

For reconstructing the selected treatment channel relative to the patient's body a tracking wire 23 provided at its distal end with a tracking element 23a is inserted from the treatment apparatus through the connected apparatus channel 20 and the treatment channel or hollow needle 10. In a first embodiment wherein a tracking element 23a is used for reconstructing the actual location of the selected treatment channel, said tracking element 23a is a magnetic tracking element.

The displacement of the magnetic tracking element 23a results in information representing the actual orientation of the inserted hollow needle 10 with its distal end 10b positioned at a certain depth within the preselected anatomical portion 11 to be treated within the patient's body 1.

The information representing the actual orientation of the selected treatment channel 10) is compared with pre-planned orientations of hollow needles 10 inserted into the patient's body at a preplanning processing stage. Based on the comparison between the actual measured information and pre-planned information said respective hollow needle 10 is identified at which apparatus channel it is connected to.

As the location and more in particular its connection with one of said treatment channels of the treatment apparatus 8 is properly established as described above, the radiation delivery means 8 will insert the energy emitting source through said identified hollow needle 10 using the correct planning parameters as regard to locations and treatment time at each location within the hollow needle 10.

Hence—as in the prior art—by obligatory connecting each inserted hollow needle 10 unambiguously with the corresponding treatment channel of the treatment apparatus 8 human mistakes are possible, resulting in significant treatment errors. As stated above with this prior art connection principle the energy emitting source can be inserted through a wrong connected hollow needle and be positioned at incorrect locations within said needle relative to the patient's body and perform radiation treatment in said wrong locations at incorrect time intervals using falsely interpreted planning parameters.

With the identification procedure according to the invention knowledge about the identity of each applicator channel of the treatment apparatus 8 to which each treatment channel/hollow needle 10 is connected is no longer required. By reconstructing the actual location of each inserted treatment channel 10 relative to the patient's body by guiding a magnetic tracking element 23a with a guiding wire 23 through the apparatus channel 20 and the selected treatment channel 10 connected therewith a proper identification of the treatment channel 10 relative to the patient's body can be obtained as well as the identification of the apparatus channel 20 to which it is connected.

When performing the therapy treatment using each properly identified treatment channel 10, the treatment apparatus and more in particular the radiation delivery means 8 can be properly operated by using the preplanned treatment parameters (dwell positions and dwell times) of the energy emitting source for the correctly identified treatment channel or hollow needle 10.

In FIG. 1 a specific embodiment of the apparatus according to the invention is disclosed. The treatment apparatus comprises a treatment planning unit 12 as well as radiation delivery means 8 comprising a robotic arm 20 provided with a connection 22, which can be brought in contact with the proximal end 10a of a selected treatment channel 10 which is inserted into a pre-selected target tissue 11, for example the prostate gland within the patient's body 1.

To this end first imaging means 2 are present, e.g. an ultrasound imaging probe to be inserted into the rectum of the patient, to obtain relevant image information about the target tissue within the patient's body. Said image information is fed via signal line 3 to the treatment planning unit 12.

For identifying each treatment channel 10 inserted with their distal end 10b inside the patient's body using the identification procedure according to the method of the invention second imaging means 50 are present for visualizing the proximal end 10a of the selected treatment channel 10 exposing outside the patient's body 1. Image information generated by said second imaging means 50 is fed through the signal line 51 to the treatment apparatus 12 and based on said image information the robotic arm 20 and the connecting element 22 is brought in alignment with the exposed proximal end 10a of the selected treatment channel 10.

The connecting element 22 is provided with a through bore 22a extending into an insertion of apparatus channel 20 which apparatus channel 20 is connected with radiation delivery means B. Moreover, the connecting element 22 is provided with sensing elements 22b-24 for sensing the presence of the exposed proximal end 10a of the selected hollow needle 10 and connecting it to the apparatus channel.

The movement of the robotic arm 20 is monitored and operated using the image information generated by the second imaging means 50 until the connecting element 22 is brought in alignment and in contact with the exposed end 10a of the hollow needle 10. Subsequent a tracking wire 23 is guided through the insertion channel 20 towards the hollow needle 10 interconnected with the connecting element 22. At the distal end of the tracking wire 23 a tracking element 23a is present, which is preferably a magnetic tracking element.

The displacement of the magnetic tracking element 23a through the selected hollow needle 10 can be reconstructed. The movement of the magnetic tracking element 23a through the hollow needle 10 and through the established magnetic field 42 results in a reconstruction of the treatment channel coordinates. The reconstructed position coordinates result in an information signal which is fed through the signal line 41 towards the treatment apparatus 12-8.

The information signal represents the actual orientation of the hollow needle 10, which reconstructed orientation or location is compared with the pre-planned orientations of the plurality of hollow needles 10-10'-etc. which are to be inserted into the patient's body upon performing the radiation treatment. After comparing using a matching algorithm the reconstructed orientation of the hollow needle 10 with the plurality of pre-planned orientations by the treatment planning unit a proper identification of the selected hollow needle 10 is obtained.

Subsequently the tracking wire 23 with the tracking element 23a is retracted from the hollow needle 10 into the treatment apparatus 8-12 and a guiding wire 61 with at its distal end an energy emitting source 60 (a HDR or LDR source) is advanced through the connecting element 22 and the hollow needle 10 for performing radiation therapy treatment at different dwell locations and dwell intervals using the correct pre-planned treatment parameters corresponding to the properly identified hollow needle 10.

Subsequent the guiding wire 61 and the energy emitting source 60 is retracted back into the treatment apparatus 8-12, the connecting element 22 is disconnected from the needle 10 and brought in alignment with a further hollow needle 10' inserted at a different location inside the patient's body 1 using the second imaging means 50.

Again, a comparison between the reconstructed orientation with the preplanned orientations is performed and based on said comparison the guiding wire 61 and the energy emitting source 60 is advanced towards the hollow needle 10' and the energy emitting source 60 is positioned at the correct dwell positions and at the correct dwell intervals using the correct preplanned therapy parameters corresponding with the properly identified hollow needle 10'.

Yet another embodiment is enclosed in FIG. 2 wherein also needles or catheter tubes 10-10' are inserted into the patient's body and which are interconnected by means of a template 5. In a similar way as disclosed in the description of FIG. 1 a robotic arm 30 is connected to the treatment apparatus 8-12 by means of the insertion channel 20. Using the imaging means 50 (see FIG. 1) the robotic arm 30 is connected with its free end 22a to each needle or catheter tube 10-10' accommodated in template 5.

In FIG. 3 a mare complicated embodiment of assistant according to the invention is disclosed, wherein the system is accommodated in a special ring shaped frame 60. More in particular all essential components of the system according to the invention are accommodated in said special ring shaped frame 60. The treatment apparatus 8-12, the robotic arm 30, the magnetic field generating means 40 (for using the magnetic tracking element) and the second imaging means 50 for imaging for example using a laser beam 50a the location of a part of the inserted treatment channels extending out of the patient's body 1 are accommodated in the ring shaped frame 60.

Also the first imaging means 5 for obtaining relevant image information about the target tissue within the patient's body are accommodated in the ring shaped frame 60.

A detector 90 is present to detect the necessary image information and to fed the thus generated image signals to the treatment apparatus 8-12.

As described above the treatment apparatus 8-12 is provided with a single channel connecting module 22 and which also forms an integrated part of the ring shaped frame device 60. It is also possible in an embodiment to integrated the robotic arm 30 in the treatment apparatus and to provide it with a single channel connecting module 22.

Furthermore the special ring shaped frame 60 is provided with a patient's table 61 on which the patient 1 is positioned and which table can be displaced in three orthogonal directions. The treatment apparatus 8-12 (for example the after loader) is connected through the insertion channel 20 with the robotic arm 30 and the hollow needle 10 placed inside the patient's body.

In a likewise manner the correct location and orientation of the hollow needles 10 inserted into the patient's body are localized and identified using a tracking wire and a tracking element inserted via the guidance channel 20 and the robotic arm 30 into each hollow needle 10 which displacement of the tracking element is determined.

For performing the radiation treatment each location of the hollow needle thus identified is correctly visualized using the second imaging means 50. Subsequently the robotic arm 30 is controlled in such a manner that the insertion channel 20 is connected to the correct hollow needle 10 and the treatment apparatus 8-12 is controlled in the correct manner by inserting the correct energy emitting source through the insertion channel 20 towards the correct hollow needle 10 into the patient's body.

The invention claimed is:

1. A computer-implemented method for identifying a first of a plurality of treatment channels configured to be inserted within a portion of a patient, at least the first treatment channel configured to be connected to an apparatus element of a treatment apparatus, the method comprising:
   receiving, using an interface, input indicating the first treatment channel, having a distal end away from the patient and configured to be connected with the apparatus element;
   reconstructing in memory, using at least one processor, an orientation, relative to the patient, of the first treatment channel connected at the distal end to the apparatus element, wherein the orientation of the first treatment channel is reconstructed by sending a tracking element to a known dwell position within the first treatment channel to produce a data record that associates the known dwell position with a three-dimensional position in space;
   comparing, using at least one processor, the reconstructed orientation with digitized pre-planned orientations of the first treatment channel to produce a comparison; and
   identifying, using at least one processor and based on the comparison, the first treatment channel as a confirmed treatment channel for treatment of the patient.

2. The computer-implemented method of claim 1, wherein reconstructing the orientation comprises vision techniques to connect the apparatus element to the distal end of the first treatment channel.

3. The computer-implemented method of claim 2, wherein reconstructing the orientation further comprises displacing the tracking element through the first treatment channel.

4. The computer-implemented method of claim 3, wherein the tracking element is a magnetic element configured to be displaced through a magnetic field.

5. The computer-implemented method of claim 1, wherein the plurality of treatment channels inserted within the portion of the patient are inserted through the use of a template.

6. The computer-implemented method of claim 1, wherein the reconstructed orientation of the first treatment channel represents the actual orientation of the first treatment channel as inserted within the patient.

7. The computer-implemented method of claim 1, wherein the treatment apparatus is configured to effect radiation treatment through the connected apparatus element and the first treatment channel based on pre-planned treatment parameters.

8. The computer-implemented method of claim 1, wherein the apparatus element comprise a plurality of delivery channels configured to effect radiation treatment.

9. The computer-implemented method of claim 8, wherein each treatment channel is configured to be connected to a corresponding delivery channel.

10. The computer-implemented method of claim 1, wherein each treatment channel is configured to be connected in a sequential order to a delivery channel within the apparatus element.

11. A system to effect radiation treatment on a patient, comprising:
   a processor configured to generate and execute a radiation treatment plan;
   a plurality of hollow treatment channels configured to be inserted into a portion of the patient based on the radiation treatment plan;

a movable apparatus element configured to connect to a first of the plurality of hollow treatment channels to deliver radiation treatment, the moveable apparatus element including a tracking element;

a sensor configured to detect the tracking element and to provide tracking element data associated with the tracking element to the processor;

the processor configured to:
monitor the tracking element, based on the tracking element data, when the moveable apparatus element is connected to the distal end of the first treatment channel;

record a three-dimensional position in space when the tracking element reaches a known dwell position;

reconstruct, based on the monitoring, an orientation of the first of the plurality of hollow treatment channels relative to the patient by associating the known dwell position with the three-dimensional position in space to generate a reconstructed orientation;

compare the reconstructed orientation with the radiation treatment plan to produce a comparison; and identify, based on the comparison, the first treatment channel as a confirmed treatment channel.

12. The system of claim 11, further comprising a radiation delivery device configured to deliver, when the moveable apparatus element is connected to the first treatment channel, radiation to the patient through the moveable apparatus element and the first treatment channel based on the radiation treatment plan.

13. The system of claim 11, wherein the radiation treatment plan comprises a pre-planned orientation of each treatment channel, a position and direction for inserting each treatment channel into the patient, and a dosage amount to be delivered by each treatment channel.

14. The system of claim 11, wherein the tracking element is located at a distal end of a tracking wire and the tracking element is configured to be displaced through the first treatment channel.

15. The system of claim 14, wherein the processor is configured to reconstruct the orientation of the first treatment channel by monitoring the displacement of tracking element.

16. The system of claim 14, further comprising a magnetic field generating device configured to establish a magnetic field around the portion of the patient.

17. The system of claim 16, wherein the tracking element includes a magnetic tracking element configured to induce a signal during the displacement of the tracking element through the magnetic field.

18. The system of claim 11, wherein the moveable apparatus element comprises a plurality of delivery channels configured to effect radiation treatment.

19. The system of claim 11, wherein each of the plurality of hollow treatment channels is configured to be connected to a corresponding delivery channel.

20. The system of claim 11, wherein each of the plurality of hollow treatment channels is configured to be connected automatically in a sequential order with a delivery channel within the moveable apparatus element.

* * * * *